United States Patent [19]
Takagi et al.

[11] Patent Number: 5,975,701
[45] Date of Patent: Nov. 2, 1999

[54] OPHTHALMOLOGIC APPARATUS

[75] Inventors: Akinari Takagi; Hiroshi Iijima, both of Tokyo, Japan

[73] Assignee: Kabushiki Kaisha Topcon, Tokyo, Japan

[21] Appl. No.: 09/076,893

[22] Filed: May 13, 1998

[30] Foreign Application Priority Data

May 14, 1997 [JP] Japan .................................. 9-123898

[51] Int. Cl.⁶ ....................................................... A61B 3/10
[52] U.S. Cl. ............................................................ 351/221
[58] Field of Search ................................... 351/205, 206, 351/208, 211, 212, 214, 246, 221

[56] References Cited

U.S. PATENT DOCUMENTS

| 4,019,813 | 4/1977 | Cornsweet et al. | 351/212 |
| 4,810,085 | 3/1989 | Fukuma et al. | 351/212 |
| 5,349,398 | 9/1994 | Koester | 351/212 |

FOREIGN PATENT DOCUMENTS

6-304144   11/1994   Japan .

*Primary Examiner*—George Manuel
*Attorney, Agent, or Firm*—Finnegan, Henderson, Farabow, Garrett & Dunner, L.L.P.

[57] ABSTRACT

An ophthalmologic apparatus is provided which comprises a slit light projecting optical system (60) for projecting a slit beam of light from an oblique direction onto the cornea (C) of a subject's eye, a light receiving optical system (70) for receiving light reflected by the cornea (C), a corneal thickness measuring circuit (74) for measuring the thickness of the cornea from information on the received light of the light receiving optical system (70), an index light projecting optical system (90) for projecting from an oblique direction onto the cornea (C) an index beam of light having a larger width than the slit beam, and a line sensor (72) for receiving the index beam reflected by the cornea (C).

7 Claims, 11 Drawing Sheets

OPHTHALMOLOGIC APPARATUS

BACKGROUND OF THE INVENTION

1. Field of the Invention

This invention relates to an ophthalmologic apparatus comprising a slit light projecting optical system for projecting a slit beam of light onto the cornea of a subject's eye and means for measuring the thickness of the cornea.

2. Description of the Related Art

Conventionally, an ophthalmologic apparatus has been known which comprises a slit light projecting optical system for obliquely projecting a slit beam of light onto the cornea of a subject's eye and a light receiving optical system for receiving light rays reflected from the cornea and which measures the thickness of the cornea according to received-light information of the light receiving optical system.

This type of ophthalmologic apparatus not only measures the thickness of the cornea according to the received light information but also calculates the distance between the cornea and a body of the apparatus according to the received light information so as to adjust alignment of a mechanical optical axis (in Z-direction) of the apparatus body (Japanese Patent Application No. Hei 5-99641).

However, in this ophthalmologic apparatus, a slit beam of light is used both for alignment in Z-direction and for measurement of the thickness of the cornea and, in addition, the width of the slit beam is made smaller to correctly measure the corneal thickness. Therefore, large disalignment (i.e., large positional deviation) of the mechanical optical axis of the apparatus body with respect to the cornea causes large deviation of the cornea-reflected light rays from a normal reflected direction. This makes it impossible that a photosensor of the light receiving optical system receives the reflected light rays. Accordingly, there is a disadvantage in that the direction in which the apparatus body is out of alignment cannot be detected, and thus the apparatus body cannot be quickly moved in an appropriate direction.

SUMMARY OF THE INVENTION

An object of the present invention is to provide an ophthalmologic apparatus which is capable of detecting the direction of disalignment when a body of the apparatus has been largely disaligned with respect to the cornea of a subject's eye in Z-direction.

An ophthalmologic apparatus according to an aspect of the present invention comprises a slit light projecting optical system for projecting a slit beam of light for measuring the corneal thickness from an oblique direction onto the cornea of a subject's eye wherein reflected rays of the slit beam reflected by the eye are received and the thickness of the cornea is measured according to information on the received rays, and an index light projecting optical system for projecting an index beam of light having a larger width than that of the slit beam of the slit light projecting optical system from an oblique direction onto the cornea. In this apparatus, the reflected rays of the index beam from the eye are received and, according to information on the received rays, the distance between the cornea and the apparatus body is calculated.

Further, an ophthalmologic apparatus according to another aspect of the present invention comprises a slit light projecting optical system for projecting a slit beam of light from an oblique direction onto the cornea of a subject's eye via a first slit plate wherein the reflected rays of the slit beam from the eye are received and, according to information on the received rays, the adjustment of alignment in a direction of a mechanical optical axis is conducted. In this apparatus, a second slit plate having a smaller slit width than the first slit plate is substituted for the first slit plate after the alignment has been completed, a slit beam of light is then projected via the second slit plate, and the reflected rays of the slit beam of the second slit plate from the eye are received and, according to information on the received rays, the thickness of the cornea is measured.

DETAILED DESCRIPTION OF THE PREFERRED EMBODIMENTS

Embodiments of an ophthalmologic apparatus according to the present invention will be described hereinafter with reference to the attached drawings.

First Embodiment

Figure 1:
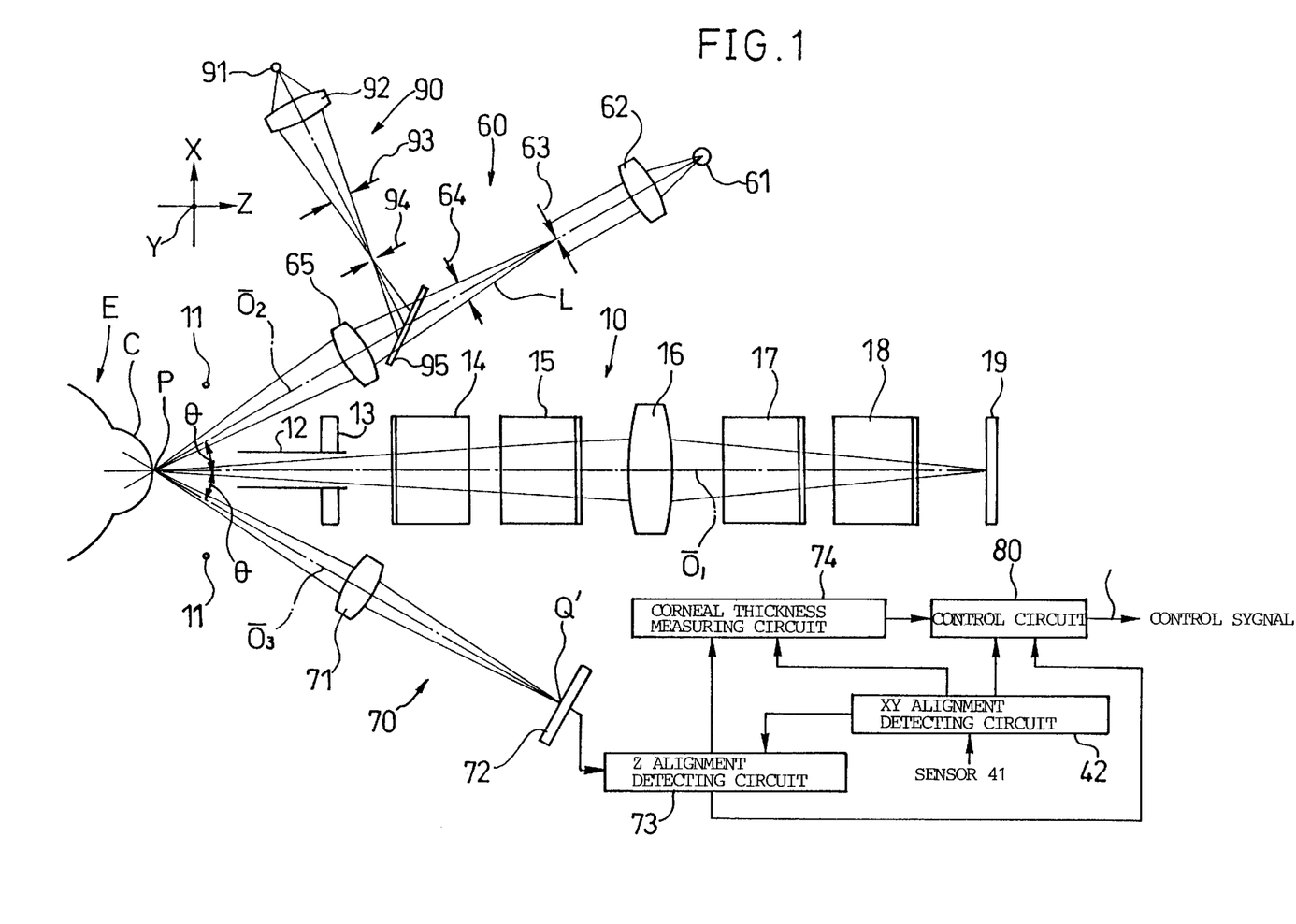
FIG. 1 is a plan view showing the arrangement of optical systems of an ophthalmologic apparatus according to the present invention.
Figure 2:
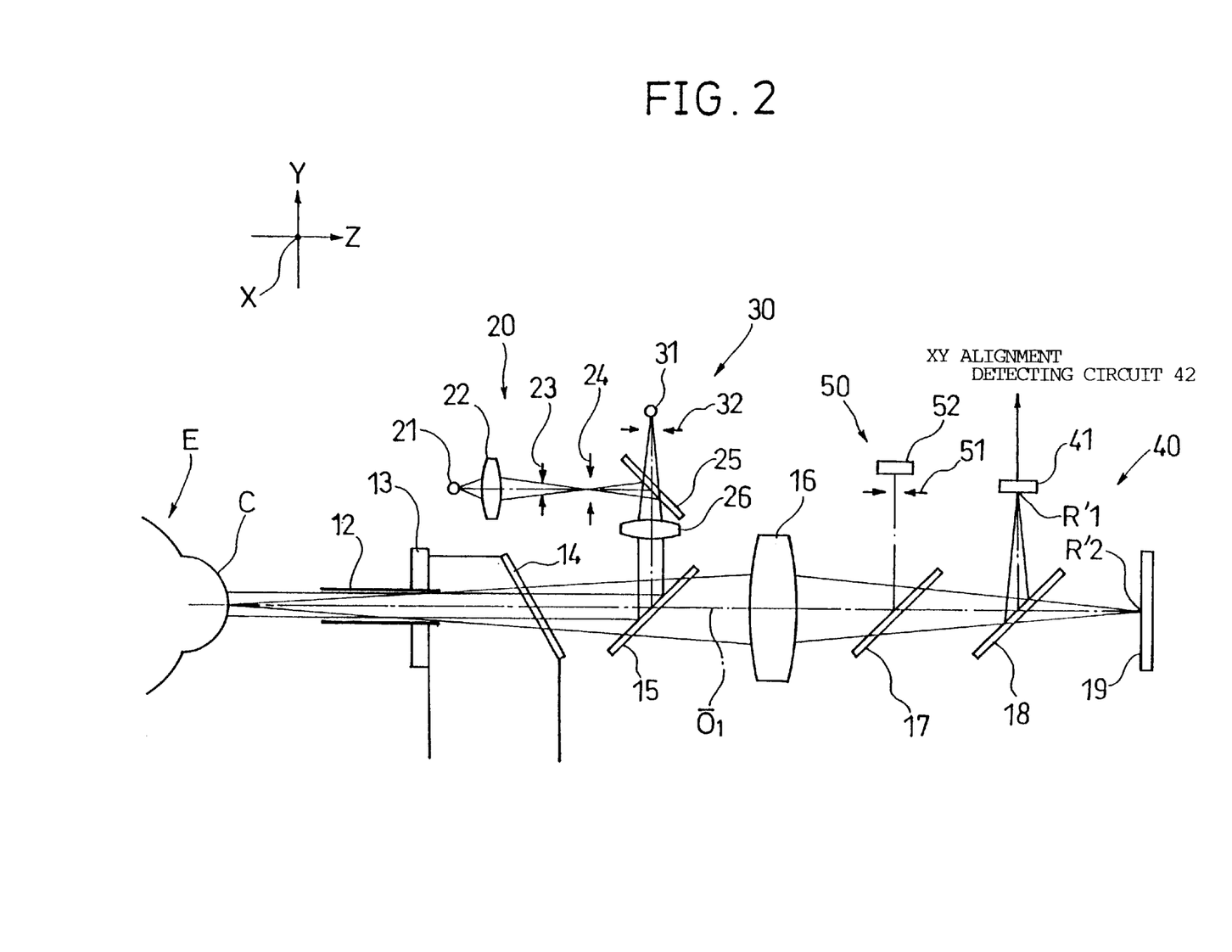
FIG. 2 is a side view of the optical systems of the ophthalmologic apparatus of FIG. 1.

FIGS. 1 and 2 each show the optical arrangement of optical systems of an ophthalmologic apparatus. The optical systems of the apparatus are disposed within an apparatus body 115 (see FIG. 7).

In FIGS. 1 and 2, reference character 10 denotes an optical system for observing the front part of a subject's eye E, reference character 20 denotes an XY alignment index light projecting optical system for frontally projecting onto the cornea C of the eye E an index beam of light used to detect alignment in an XY-direction (in a direction perpendicular to an axis O1) and detect the deformation of the cornea, reference character 30 denotes a fixing target projecting optical system for projecting a fixing target, on which the eye is fixed, onto the eye E, reference character 40 denotes an XY alignment detecting optical system for receiving the light rays reflected from the cornea C of the XY alignment index beam and detecting the positional relationship in the XY-direction between the apparatus body 115 and the cornea C, reference character 50 denotes a corneal deformation detecting optical system for receiving the light rays reflected from the cornea C of the XY alignment index beam and detecting the quantity of deformation of the cornea C, reference character 60 denotes a slit light projecting optical system for projecting a slit beam of light having a small width from an oblique direction onto the cornea C, reference character 90 denotes an index light projecting optical system for projecting an index beam of light having a larger width than that of the slit beam from an oblique direction onto the cornea C so as to detect alignment in a Z-direction (in a direction of the axis O1), reference character 70 denotes a light receiving optical system for receiving the light rays reflected by the cornea C of the index beam or the slit beam from a direction symmetrical with respect to the optical axis of the eye's front observing optical system 10.

The eye's front observing optical system 10 comprises a plurality of light sources 11 which are situated on the right and left sides of the eye E and which directly illuminate the front part of the eye E, a gas jetting nozzle 12, a window glass 13 for the front of the eye E, a chamber window glass 14, a half mirror 15, an objective lens 16, half mirrors 17, 18, and a CCD camera 19. Reference character O1 denotes the optical axis of the eye's front observing optical system 10.

An image of the front part of the eye E illuminated by the eye's front illuminating light sources 11 passes through the inside and outside of the gas jetting nozzle 12, then passes through the window glass 13, the chamber window glass 14 and the half mirror 15, then passes through the half mirrors 17, 18 while being converged by the objective lens 16, and is formed on the CCD camera 19. A puff of air is jetted out from the nozzle 12 onto the eye E by gas jetting means (not shown). A tonometer is mainly made up of the nozzle 12, the gas jetting means, and the corneal deformation detecting optical system.

The XY alignment index light projecting optical system comprises a light source 21 which emits infrared light and is used for XY alignment, a condenser lens 22, an aperture diaphragm 23, a pinhole plate 24, a dichroic mirror 25, a projection lens 26 situated on an optical path so as to be focused on the pinhole plate 24, the half mirror 15, the chamber window glass 14, and the gas jetting nozzle 12.

Figure 3:
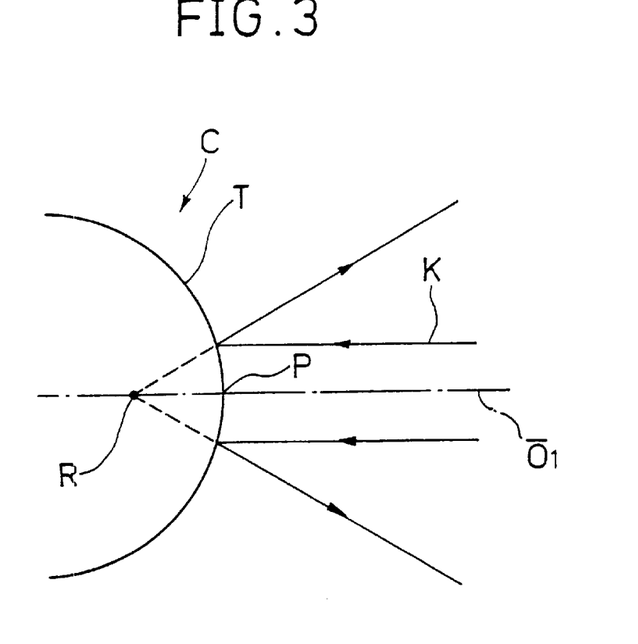
FIG. 3 is an explanatory drawing showing how an alignment beam of light frontally projected onto the cornea is reflected.

The infrared light emitted from the XY alignment light source 21 passes through the aperture diaphragm 23 while being converged by the condenser lens 22, and reaches the pinhole plate 24. The light beam which has passed through the pinhole plate 24 is reflected by the dichroic mirror 25, is then turned into parallel rays of light by the projection lens 26 and is reflected by the half mirror 15, and thereafter passes through the chamber window glass 14 and the inside of the gas jetting nozzle 12, and, as shown in FIG. 3, is turned into an XY alignment index beam K. In FIG. 3, the XY alignment index beam K is reflected by a corneal surface T so as to form a luminance point image R between the vertex P of the cornea C and the curvature center of the cornea C. The aperture diaphragm 23 is in a position conjugate to the vertex P with respect to the projection lens 26.

The fixing target projecting optical system 30 comprises a fixing-target light source 31 which emits visible light, a pinhole plate 32, the dichroic mirror 25, the projection lens 26, the half mirror 15, the chamber window glass 14, and the gas jetting nozzle 12.

A fixing-target beam emitted from the light source 31 is turned into parallel rays of light by the projection lens 26 via the pinhole plate 32 and the dichroic minor 25, is then reflected by the half mirror 15, then passes through the chamber window glass 14 and the inside of the gas jetting nozzle 12, and is guided to the eye E. A subject gazes fixedly at the fixing target, so that the subject's eye is fixed thereon.

The XY alignment detecting optical system comprises the gas jetting nozzle 12, the chamber window glass 14, the half mirror 15, the objective lens 16, the half mirrors 17, 18, a sensor 41, and an XY alignment detecting circuit 42.

The light beam which has been projected onto the cornea C by the XY alignment index light projecting optical system 20 and has been reflected on the corneal surface T passes through the inside of the nozzle 12, and then passes through the chamber window glass 14 and the half mirror 15. Thereafter, a part of the beam passes through the half mirror 17, and a part of the transmitted part is reflected by the half mirror 18 while being converged by the objective lens 16. The light reflected by the half mirror 18 forms a luminance point image R'1 on the sensor 41. The sensor 41 is a photosensor capable of detecting a position, such as a PSD. The XY alignment detecting circuit 42 calculates the positional relationship (in the XY-direction) between the apparatus body 115 and the cornea C by means of well-known means according to the output of the sensor 41, and then outputs arithmetic results to a corneal thickness measuring circuit 74 and a control circuit 80.

Figure 4:
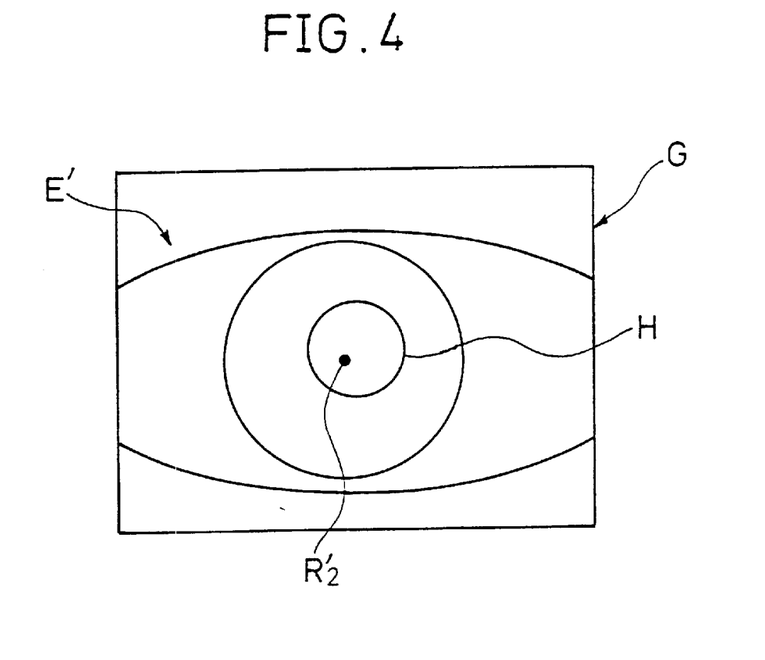
FIG. 4 is an explanatory drawing showing an image of the front part of the eye displayed on the screen of a monitor.

On the other hand, the reflected light from the cornea C which has passed through the half mirror 18 forms a luminance point image R'2 on the CCD camera 19. The CCD camera 19 outputs an image signal to a monitor unit, and, as shown in FIG. 4, an image E' of the front part of the eye E and the luminance point image R'2 of the XY alignment index beam are displayed on a screen G of the monitor unit. In FIG. 4, reference character H denotes an alignment assisting mark formed by imaging means (not shown).

The light reflected by the half mirror 17 is led to the corneal deformation detecting optical system 50, that is, to a sensor 52 through a pinhole plate 51. The sensor 52 is a photosensor capable of detecting the quantity of light, such as a photodiode.

The slit light projecting optical system 60 comprises a slit light source 61 for emitting an infrared beam of light, a condenser lens 62, a slit 63, a square aperture diaphragm 64, a half mirror 95, and a projection lens 65 situated on an optical path so as to be focused on the aperture diaphragm 64. Reference character O2 denotes an optical axis of the slit light projecting optical system 60.

Figure 5:
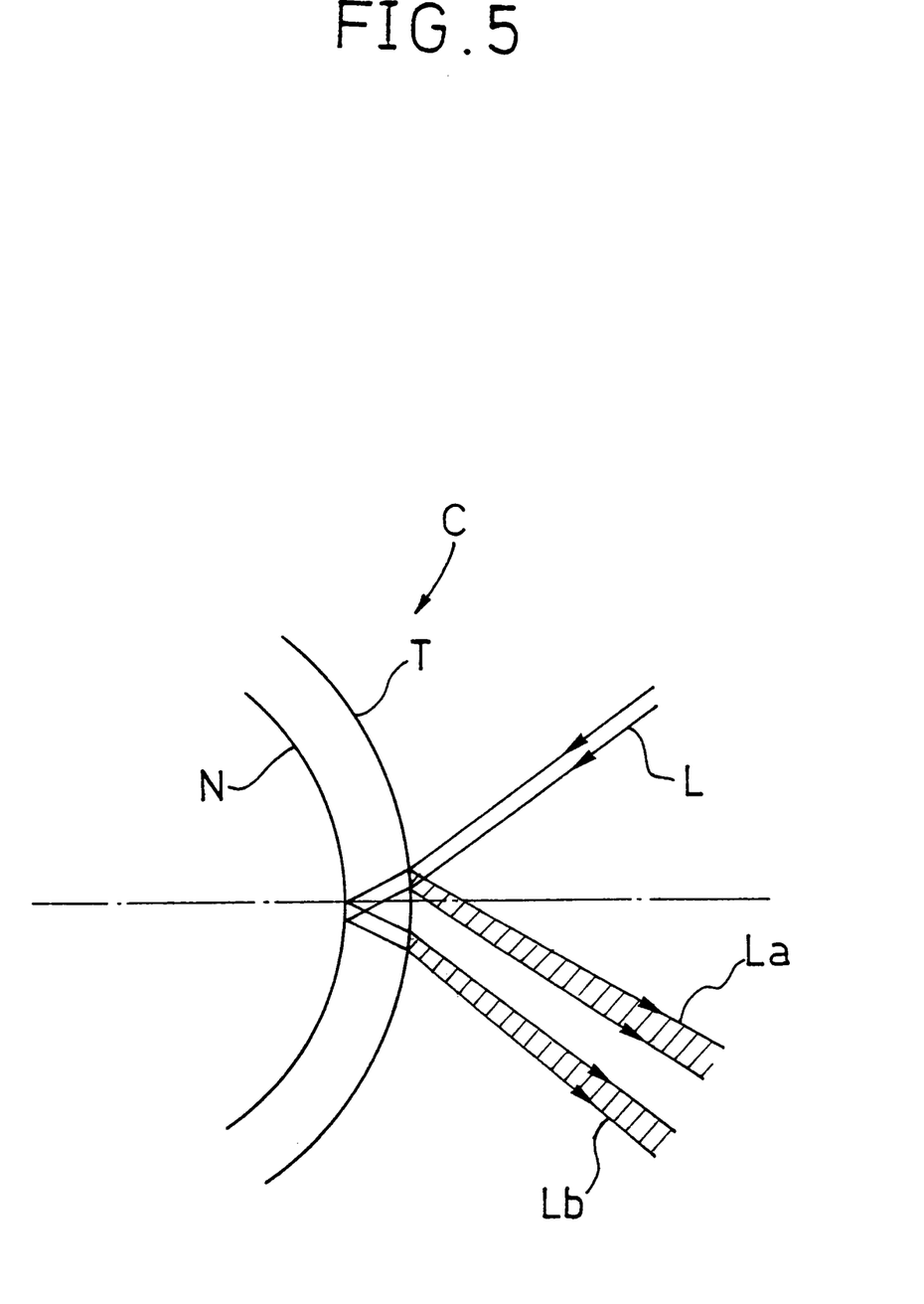
FIG. 5 is an explanatory drawing showing a case where a slit beam of light is projected from an oblique direction onto the cornea.

The infrared beam emitted from the slit light source 61 is condensed by the condenser lens 62 and is led to the slit 63. A slit beam L which has passed through the slit 63 passes through the aperture diaphragm 64 and the half mirror 95, and is projected onto the cornea C by the projection lens 65. As shown in FIG. 5, a part of the slit beam L projected onto the cornea C is reflected by the corneal surface T, i.e., by the boundary surface between the atmosphere and the cornea C, whereas the part of the slit beam L which has passed through the corneal surface T is reflected by a corneal back surface N. The quantity of light of a beam L$a$ reflected by the corneal surface T is approximately 100 times as much as that of a beam L$b$ reflected by the corneal back surface N. The slit 63 is in a position conjugate to the corneal back surface N with respect to the projection lens 65.

The light receiving optical system 70 comprises an imaging lens 71 and a line sensor 72. Reference character O3 denotes an optical axis of the light receiving optical system 70.

Figure 6A:
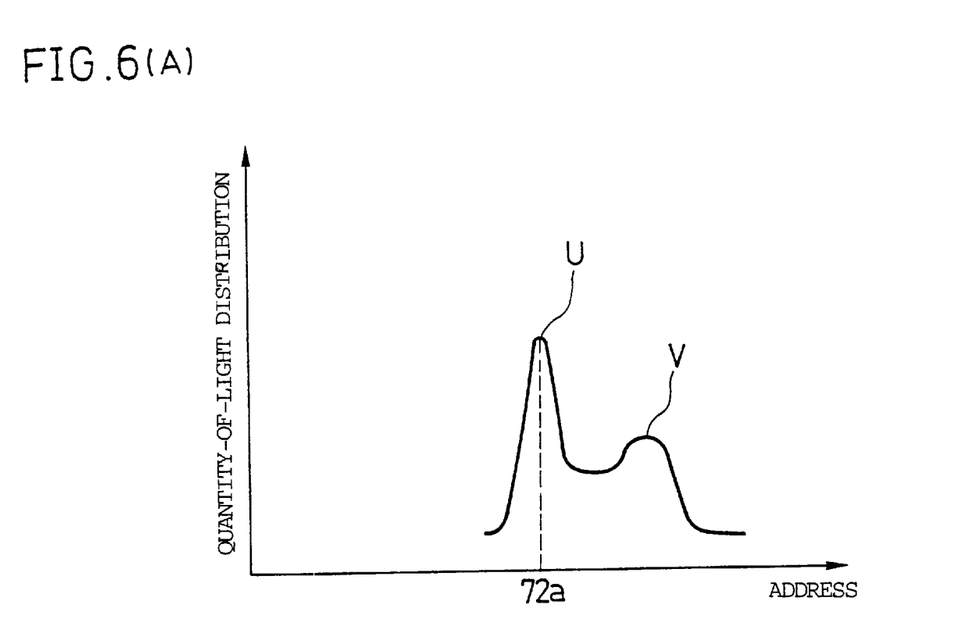
FIG. 6(A) is a graph showing a quantity-of-light distribution of a line sensor.
Figure 6B:
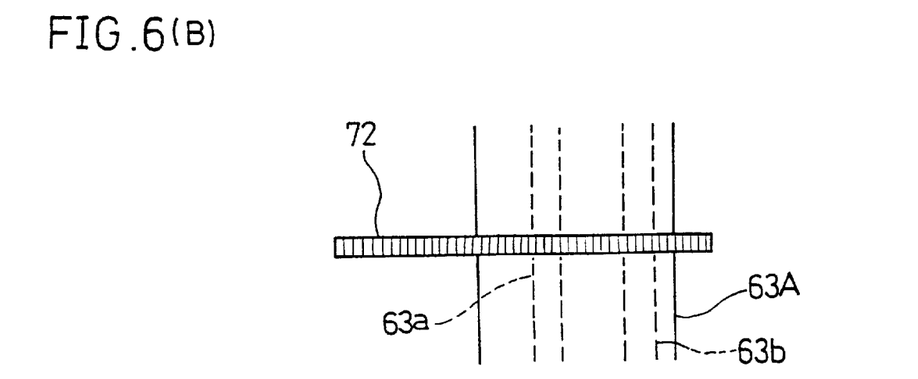
FIG. 6(B) is an explanatory drawing showing a slit image formed on the line sensor.

In the slit light projecting optical system 60, the reflected beams La, Lb of the slit beam L which have been reflected by the corneal surface T and the corneal back surface N are converged by the imaging lens 71, and thereby, as shown in FIG. 6(B), a slit image 63A is formed on the line sensor 72. The distribution of the quantity of light of the slit image 63A is shown in FIG. 6(A). In FIG. 6(A), reference character U denotes a peak of the reflected beam reflected by the corneal surface T, and reference character V denotes a peak of the reflected beam reflected by the corneal back surface N. The peak U corresponds to a light image 63a of the slit image 63A, and the peak V corresponds to a light image 63b thereof.

As shown in FIG. 1, the output at each address of the line sensor 72 is inputted to a Z alignment detecting circuit 73.

The index light projecting optical system 90 comprises a Z alignment light source 91 for emitting infrared light, a condenser lens 92, an aperture diaphragm 93, a pinhole plate 94, a half mirror 95, and a projection lens 65 situated on an optical path so as to be focused on the pinhole plate 94. The index light projecting optical system 90 projects onto the cornea C an index beam of light W (see FIG. 9) having a width larger than the beam of the slit light projecting optical system 60.

Figure 9:
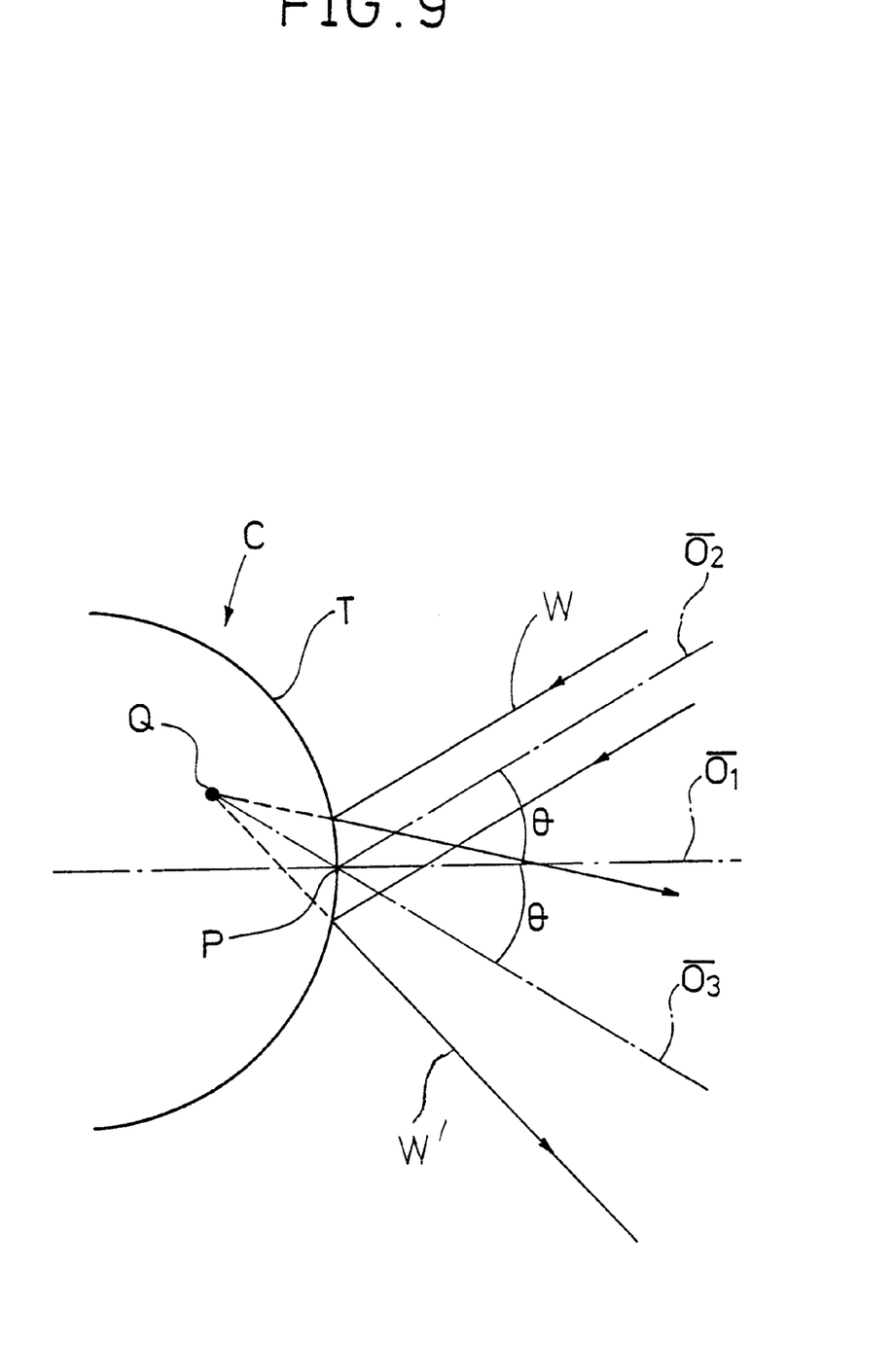
FIG. 9 is an explanatory drawing showing a relationship between the cornea and an index beam of light.

The infrared beam of light emitted from the Z alignment light source 91 is condensed by the condenser lens 92 to reach the aperture diaphragm 93, and is led to the pinhole plate 94 through the aperture diaphragm 93. The index beam W which has passed through the pinhole plate 94 is reflected by the half mirror 95, is then led to the cornea C by the projection lens 65, and, as shown in FIG. 9. is reflected by the corneal surface T so as to form a luminance point image Q. The aperture diaphragm 93 is in a position conjugate to the corneal vertex P.

The index beam W projected by the index light projecting optical system 90 is reflected by the corneal surface T to form an index-reflected beam W'. Thereafter, the index-reflected beam W' is condensed by the imaging lens 71 so as to form a luminance point image Q' on the line sensor 72.

Figure 10:
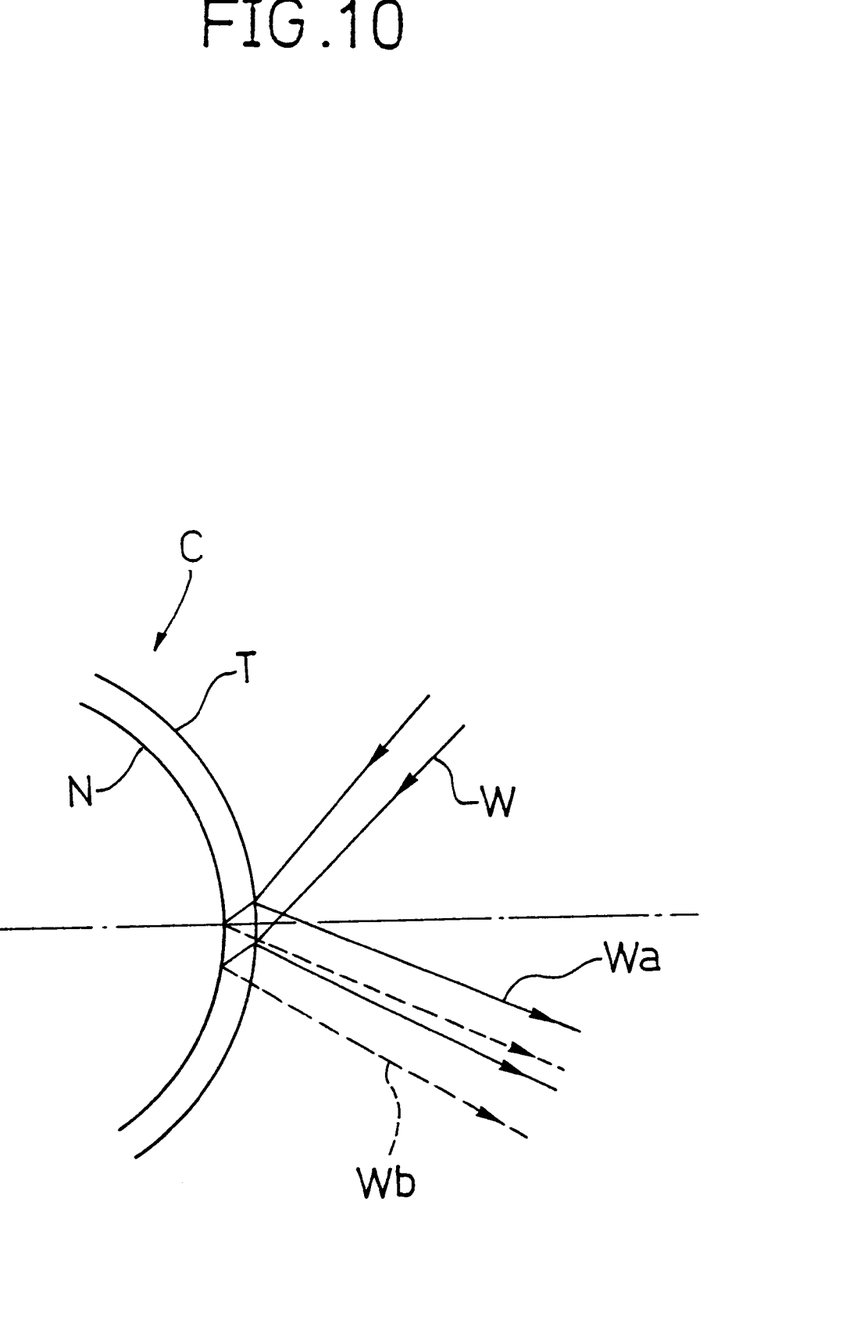
FIG. 10 is an explanatory drawing showing a case where the index beam is projected onto the cornea.
Figure 11:
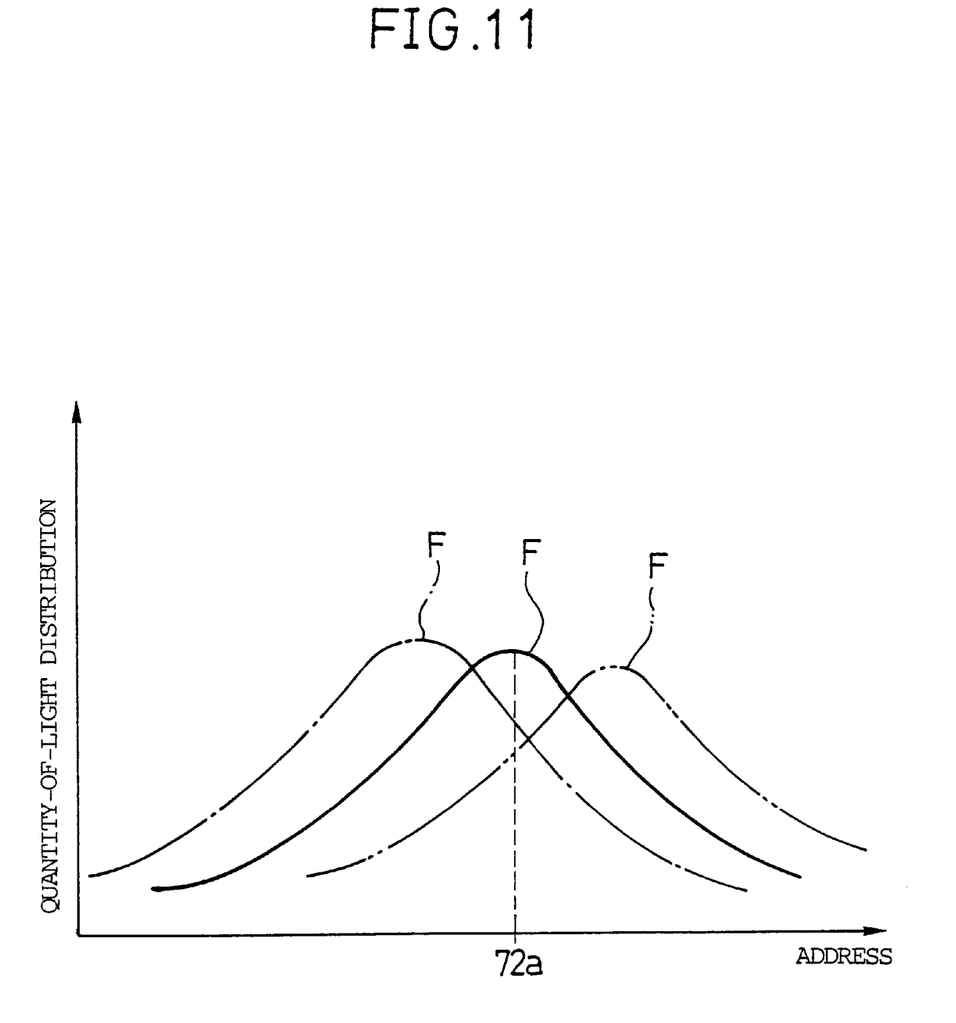
FIG. 11 is a graph showing a quantity-of-light distribution on the line sensor in the case where the index beam is projected onto the cornea.

The width of the index beam W projected onto the cornea C by the index light projecting optical system 90 is designed to be larger than that of the slit beam L by the slit light projecting optical system 60. As shown in FIG. 10, the index beam W projected onto the cornea C is reflected by the corneal surface T and the corneal back surface N, and reflected index beams of light Wa, Wb are converged by the imaging lens 71, and thereby an aperture image of the aperture diaphragm 93 is formed on the line sensor 72. In the quantity-of-light distribution of the aperture image, the quantity of the reflected beam Wa is by far larger than that of the reflected beam Wb, and thus it becomes curved lines as shown in FIG. 11. In FIG. 11, a peak point shown by reference character F represents the light quantity at the central point of the reflected beam Wa.

When the position of the peak F corresponds substantially to a reference address 72a of the line sensor 72, rough alignment in a Z-direction is set to be completed, so that the position in the 2-direction of the apparatus body 115 can be obtained by the positional information (the address information) of the peak F. The light quantity distribution is shown by an alternate long and short dash line when the apparatus body 115 is too close to the cornea C, whereas the light quantity distribution is shown by an alternate long and two short dashes line when the apparatus body 115 is too away from the cornea C.

Further, in the case where the width of the index beam W is larger than that of the beam L, the width of the reflected beam Wa becomes larger than that of the beam La or Lb. Therefore, the line sensor 72 can receive the reflected beam Wa even though the apparatus body 115 is largely out of alignment in the Z-direction.

The Z alignment detecting circuit 73 calculates the peaks U, V shown in FIG. 6(A) or the positional information (the address information) of the peak F shown in FIG. 11, and outputs the result to the control circuit 80 or the corneal thickness measuring circuit (the measuring means) 74. In the corneal thickness measuring circuit 74, the thickness of the cornea C is calculated by well-known means according to the positional information of the peaks U, V. Further, the control circuit 80 controls a motor 112 according to the positional information of the peaks U, F such that the apparatus body 115 is moved in the Z-direction to adjust the alignment in the Z-direction.

Figure 7:
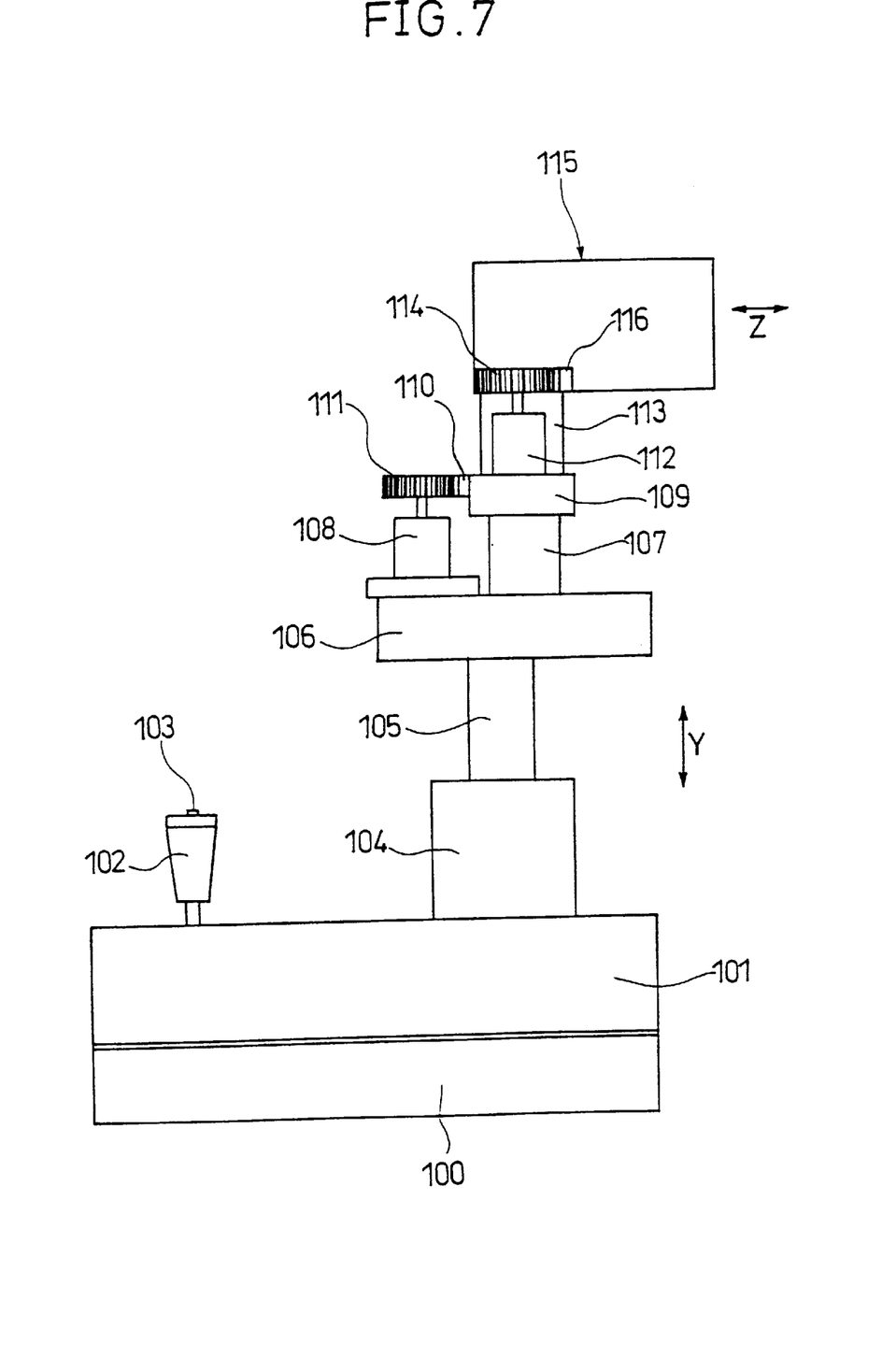
FIG. 7 is a side view of the whole ophthalmologic apparatus of FIG. 1.

FIG. 7 is a side view of the whole ophthalmologic apparatus, and reference character 100 denotes a base containing a power source. A stand 101 is attached to the upper part of the base 100 so as to be moved in front, back, right, and left directions by the operation of a control lever 102. The control lever 102 is provided with a manual switch 103 which is used in the case of a manual mode (in the first embodiment, the manual mode is used). A motor 104 and a supporting column 105 are disposed on and above the stand 101, respectively. The motor 104 is connected to the supporting column 105 by means of a pinion rack (not shown), and the supporting column 105 is moved up and down (in a Y-direction) by the motor 104. A table 106 is attached to the upper end of the supporting column 105.

Figure 8:
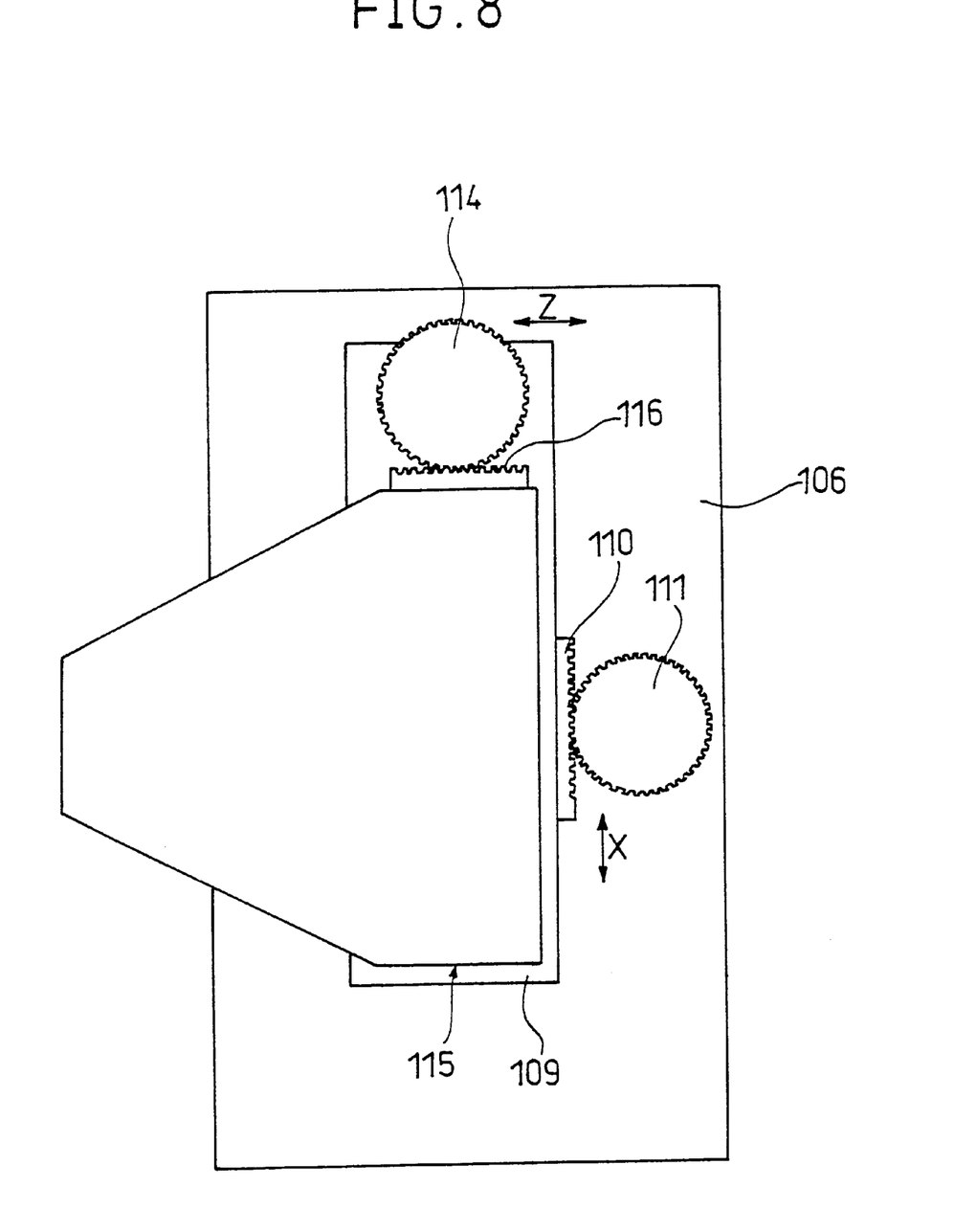
FIG. 8 is a plan view of the essential part of the ophthalmologic apparatus of FIG. 1.

A supporting column 107 and a motor 108 are attached to the table 106. A table 109 is slidably attached to the upper end of the supporting column 107. As shown in FIG. 8, a rack 110 is attached to the back end of the table 109. A pinion 111 is attached to the power shaft of the motor 108, and the pinion 111 is engaged with the rack 110. A motor 112 and a supporting column 113 are attached to the upper part of the table 109. A pinion 114 is attached to the power shaft of the motor 112. The apparatus body 115 is slidably attached to the upper part of the supporting column 113. A rack 116 is attached to the side part of the apparatus body 115. The rack 116 is engaged with the pinion 114. The optical systems shown in FIG. 1 and FIG. 2 are contained in the apparatus body 115.

The motors 104, 108, 112 are controlled by a control signal outputted by the control circuit 80. The movement in the Y-direction of the apparatus body 115 is controlled when the control signal is outputted to the motor 104, the movement in the X-direction thereof is controlled when the control signal is outputted to the motor 108, and the movement in the Z-direction thereof is controlled when the control signal is outputted to the motor 112. Thus, alignment is automatically adjusted.

Next, an explanation will be made of the operation of the ophthalmologic apparatus in the aforementioned embodiment.

First, the fixing of the eye is performed by turning on the light source 31 of the fixing target projecting optical system 30, and the Z alignment light source 91 of the index light projecting optical system 90 is turned on. Thereafter, the operator conducts rough alignment while observing the image E' of the front part of the subject on the screen G of the monitor using the eye's front observing optical system 10. At this time, the XY alignment detecting circuit 42 and the Z alignment detecting circuit 73 calculate a relative position of the apparatus body 115 to the cornea C according to the output of the sensor 41 of the XY alignment detecting optical system and the output of the line sensor 72 of the light receiving optical system 70. The calculated position is displayed on the screen (informing means) G of the monitor, in order to inform the operator of the result. At this time, the light source 61 of the slit light projecting optical system 60 is kept off.

The position in the Z-direction of the apparatus body 115 is obtained according to the positional information of the peak F outputted by the Z alignment detecting circuit 73 as shown in FIG. 11. Since the width of the reflected beam W$a$ is large, the line sensor 72 receives the reflected beam W$a$ even though disalignment in the Z-direction is large. Therefore, the position in the Z-direction of the apparatus body 115, that is, the direction of a positional deviation, is detected, and the direction in which the apparatus body 115 should be moved or the position in the Z-direction of the apparatus body 115 can be displayed on the screen G. This makes it possible to quickly move the apparatus body 115 in an appropriate direction in which alignment is adjusted.

When the operator slightly moves the stand 101 according to the display on the screen G, the control circuit 80 allows the apparatus body 115 to move in the direction of the alignment by controlling the drive of the motors 104, 108, 112. A determination of whether the stand 101 has moved or not is made according to variations in the output of the line sensor 72, that is, variations in the output of the Z alignment detecting circuit 73.

When rough alignment of the apparatus body 115 with respect to the cornea C is conducted by controlling the drive of each motor 104, 108, 112 of the control circuit 80, in other words, when the luminance point image R'2 on the screen G of the monitor is situated in the middle of the alignment assisting mark H and the peak F shown in FIG. 11 is situated close to the reference address 72$a$ of the line sensor 72, the Z alignment light source 91 of the index light projecting optical system 90 is turned off, and the light source 61 of the slit light projecting optical system 60 is turned on.

Immediately before the Z alignment light source 91 is turned off, the Z alignment detecting circuit 73 calculates a position in the Z-direction of the apparatus body 115 according to the output of the line sensor 72 when the peak F shown in FIG. 11 is situated close to the reference address 72$a$ of the line sensor 72, and the control circuit 80 controls the motor 112 according to the calculated position and moves the apparatus body 115 in the Z-direction.

When the light source 61 of the slit light projecting optical system 60 is turned on, as shown in FIG. 6(B), the slit image 63A is formed on the line sensor 72, and alignment in the Z-direction is conducted according to the light quantity distribution of the slit image 63A. In other words, the apparatus body 115 is moved in a direction in which the peak U shown in FIG. 6(A) corresponds to the reference address 72$a$ of the line sensor 72. When the peak U corresponds to the reference address 72$a$ of the line sensor 72, that is, when the alignment in the Z-direction is completed, the corneal thickness measuring circuit 74 measures the thickness of the cornea C according to the positional information of the peaks U, V which is outputted by the Z alignment detecting circuit 73 according to the output of the line sensor 72.

Simultaneously with the calculations, a puff of air is jetted from the nozzle 12 onto the cornea C, and thereby the cornea C is pressed and flattened. At this time, the quantity of deformation of the cornea C is detected by the corneal deformation detecting optical system 50. The intraocular pressure of the eye is calculated according to the detected quantity of deformation of the cornea C and the pressure of the air puff jetted from the nozzle 12, and then the calculated intraocular pressure is compensated according to the thickness of the cornea C.

Thereafter, the thickness of the cornea C, the calculated intraocular pressure, and the compensated intraocular pressure are displayed on the screen G of the monitor.

The air puff is jetted from the nozzle 12 by air stream jetting means (not shown), and the pressure of the air puff is detected by a pressure sensor (not shown) provided in the air stream jetting means.

In the aforementioned embodiment, rough alignment is conducted by projecting the index beam W of the index light projecting optical system 90 onto the cornea C, and precise alignment is conducted by the slit light projecting optical system 60 after the Z alignment light source 91 has been turned off. However, both of the rough alignment and the precise alignment may be conducted by using the index beam W. In this case, at the same time as the completion of the precise alignment, the thickness of the cornea C, intraocular pressure, and compensated intraocular pressure are calculated by turning off the Z alignment light source 91 and turning on the light source 61 of the slit light projecting optical system 60. Preferably, the light sources 61, 91 are kept off while the intraocular pressure is calculated, in order to prevent the reflected beams L$a$, L$b$ from causing errors.

Further, in the aforementioned embodiment, there is provided the half mirror 95 by which an optical system is divided into the slit light projecting optical system 60 and the index light projecting optical system 90. However, instead of the half mirror 95, a switching mirror may be used. In this case, preferably, the switching mirror is designed to be automatically come out of the optical axis O2 at the same time as the completion of the rough alignment. However, it may come out of the optical axis O2 after the completion of the precise alignment.

Second Embodiment

Figure 12:
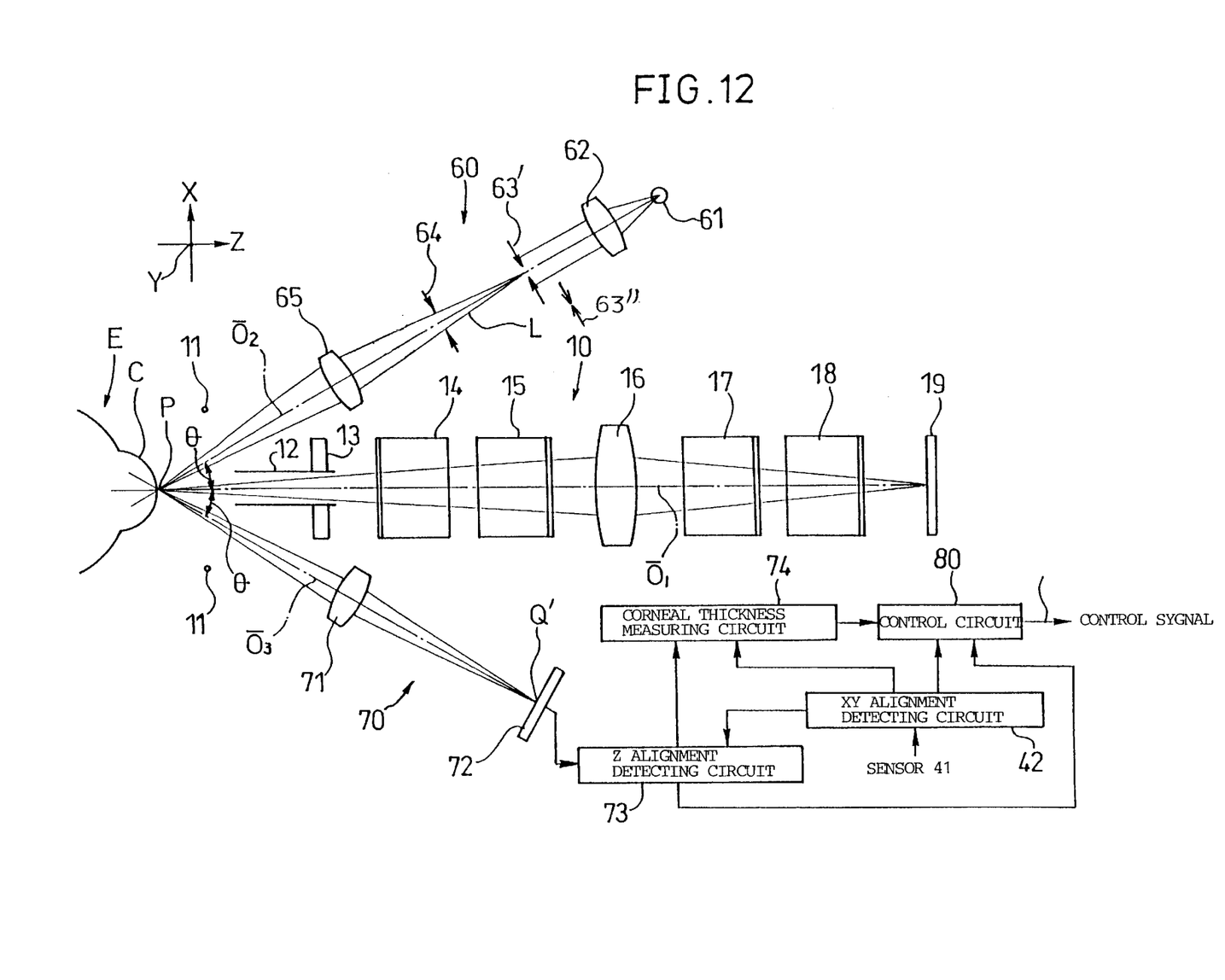
FIG. 12 is a plan view showing the arrangement of optical systems of an ophthalmologic apparatus according to a second embodiment of the present invention.

FIG. 12 shows a second embodiment. According to the second embodiment, instead of disposing the index light projecting optical system 90, a slit 63' having a large slit width and a slit 63" having a small slit width are exchangeably provided in the slit light projecting optical system 60, as shown in FIG. 12,. In other words, the slit 63' having the large slit width is used until the rough alignment is completed, and the slit 63" having the small slit width is used after the rough alignment is completed. According to this construction, the same effect as in the first embodiment can be obtained.

What is claimed is:

1. An ophthalmologic apparatus comprising:

a slit light projecting optical system for projecting from an oblique direction onto a cornea of an eye of a subject a slit beam of light for measuring a corneal thickness of the eye wherein light rays of the slit beam reflected from the eye are received and, based on information about received light rays, the thickness of the cornea is measured; and an index light projecting optical system for projecting from an oblique direction onto the cornea an index beam of light having a larger width than the slit beam of said slit light projecting optical system;

wherein light rays of the index beam reflected from the eye are received and, based on information about received light rays, a distance between the cornea and an apparatus body of said ophthalmologic apparatus is calculated.

2. An ophthalmologic apparatus according to claim 1, wherein the light rays of the slit beam reflected from the eye and the light rays of the index beam reflected from the eve are received by a single photosensor.

3. An ophthalmologic apparatus according to claim 1 or 2, further comprising movement controlling means for controlling a movement of said apparatus body according to a calculation result of the distance between the cornea and said apparatus body.

4. An ophthalmologic apparatus according to claim 1 or 2, wherein said slit light projecting optical system and said index light projecting optical system share a part of optical paths of the respective optical systems.

5. An ophthalmologic apparatus according to claim 1 or 2, wherein a light source of said index light projecting optical system is off when a light source of said slit light projecting optical system is on.

6. An ophthalmologic apparatus according to claim 1, further comprising informing means for informing an operator of the distance between the cornea and said apparatus body.

7. An ophthalmologic apparatus comprising:

a slit light projecting optical system for projecting a slit beam of light from an oblique direction onto a cornea of an eye of a subject via a slit plate wherein light rays of the slit beam reflected by the eye are received and, based on information about received light rays, alignment in a direction of a mechanical optical axis is adjusted;

wherein another slit plate having a smaller slit width than said slit plate is substituted for said slit plate after the alignment has been completed, a slit beam of light is then projected via said another slit plate, and light rays of the slit beam of said another slit plate reflected by the eye are received and, based on information about received light rays, a thickness of the cornea is measured.

\* \* \* \* \*